United States Patent [19]
Dehdashtian et al.

[11] Patent Number: 6,013,092
[45] Date of Patent: *Jan. 11, 2000

[54] FOLDING OF CATHETER-MOUNTED BALLOONS TO FACILITATE NON-ROTATIONAL RADIAL EXPANSION OF INTRALUMINAL DEVICES

[75] Inventors: Mark Dehdashtian, Costa Mesa; Maria Lilian Saravia, Garden Grove; Misuzu Sakata, Santa Ana, all of Calif.

[73] Assignee: Baxter International Inc., Deerfield, Ill.

[ * ] Notice: This patent issued on a continued prosecution application filed under 37 CFR 1.53(d), and is subject to the twenty year patent term provisions of 35 U.S.C. 154(a)(2).

[21] Appl. No.: 09/135,736

[22] Filed: Aug. 18, 1998

[51] Int. Cl.⁷ .................................................. A61M 29/00
[52] U.S. Cl. ........................... 606/194; 606/198; 606/96; 623/1
[58] Field of Search ..................................... 606/191, 194, 606/198, 200; 604/96–101; 623/1, 12

[56] References Cited

U.S. PATENT DOCUMENTS

| | | |
|---|---|---|
| 5,226,887 | 7/1993 | Farr et al. . |
| 5,318,587 | 6/1994 | Davey . |
| 5,342,307 | 8/1994 | Euteneuer et al. . |
| 5,350,361 | 9/1994 | Tsukashima et al. . |
| 5,456,666 | 10/1995 | Campbell et al. . |
| 5,458,572 | 10/1995 | Campbell et al. . |
| 5,490,839 | 2/1996 | Wang et al. . |
| 5,792,172 | 8/1998 | Fischell et al. ........................ 606/194 |

Primary Examiner—Michael Buiz
Assistant Examiner—William W. Lewis
Attorney, Agent, or Firm—Bruce M. Canter; Guy L. Cumberbatch; Peter Jon Gluck

[57] ABSTRACT

Methods for folding a catheter mounted balloon, and delivery catheter systems which incorporate radially expandable intraluminal devices (e.g., stents, grafts and stented grafts) which are mounted on a balloon folded in accordance with this method. The method comprises generally folding the balloon at least twice, in opposite directions, so that any rotational forces created by the unfolding of the balloon as it is inflated will counteract each other, and will thus avoid substantial rotational movement of the intraluminal device during its radial expansion.

40 Claims, 2 Drawing Sheets

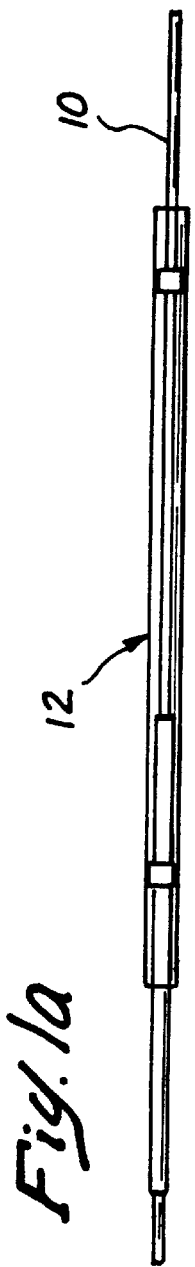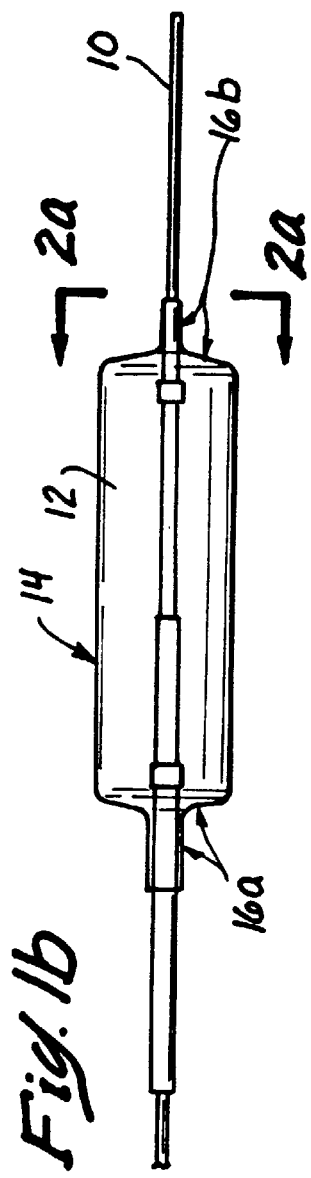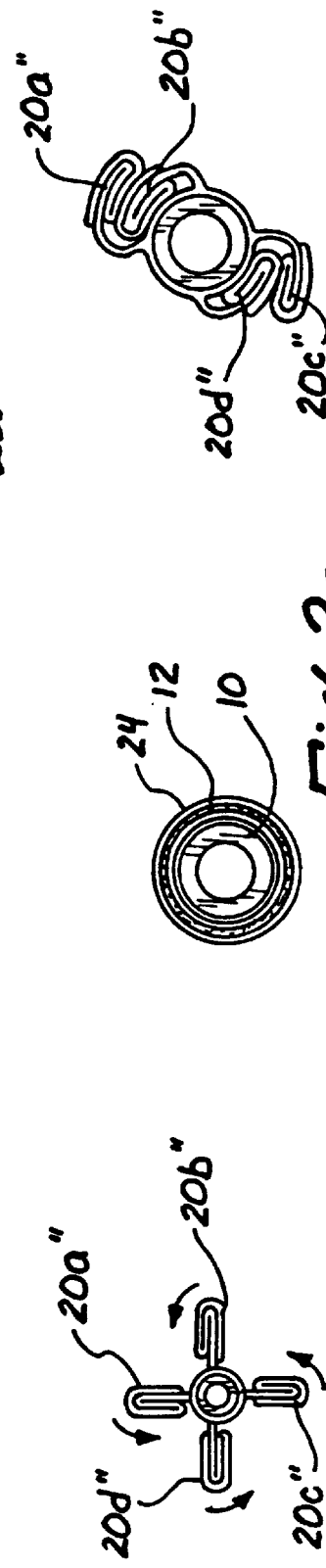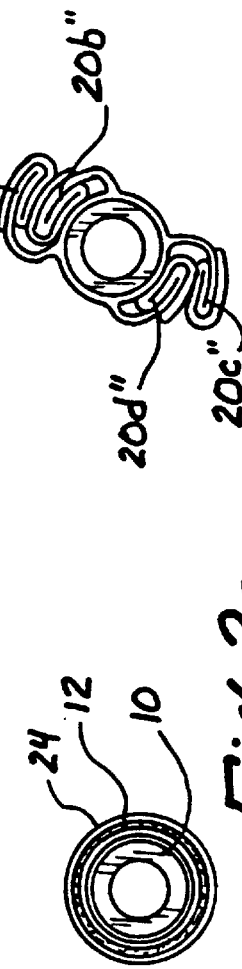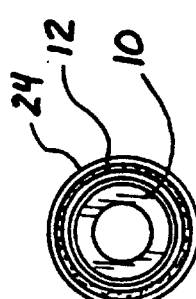

FOLDING OF CATHETER-MOUNTED BALLOONS TO FACILITATE NON-ROTATIONAL RADIAL EXPANSION OF INTRALUMINAL DEVICES

FIELD OF THE INVENTION

The present invention relates generally to medical methods and devices, and more particularly to an improved method for folding a balloon which is utilized to radially expand an intraluminal prosthetic device such as a stent or stented graft.

BACKGROUND OF THE INVENTION

In modern medical practice, various types of radially expandable endoluminal devices, such as stents and stented grafts, are frequently implanted within the lumens of blood vessels or other anatomical conduits. Typically, these endoluminal devices are initially mounted on a pliable delivery catheter while in a radially compact state, and the delivery catheter (having the radially compact endoluminal device mounted thereon) is then transluminally advanced through the vasculature or other system of anatomical passageway(s), to the location where the endoluminal device is to be implanted. Thereafter, the endoluminal device is caused to radially expand to an operative, radially expanded configuration wherein it engages the surrounding wall of the blood vessel or other anatomical conduit, frictionally holding the endoluminal device in its desired position within the body.

Many of the radially expandable endoluminal devices of the prior art have been generally classifiable in one of two (2) categories: i.e., self-expanding or pressure-expandable. Endoluminal devices of the "self-expanding" variety are usually formed of a resilient material (e.g., spring metal) or shape memory alloy, which automatically expands from a radially collapsed configuration to a radially expanded configuration, and are typically mounted on a delivery catheter which incorporates some constraining apparatus (e.g., a retractable restraining member, sheath or wall of the delivery catheter) which operates to hold the device in its radially compact state until it is desired to release the device at its site of implantation.

Endoluminal devices of the "pressure-expandable" variety are typically formed at least partially of malleable or plastically deformable material which will deform as it radially expands, and are initially formed in a radially compact configuration and mounted on a delivery catheter which incorporates a balloon or other pressure-exerting apparatus which serves to pressure-expand the endoluminal device when at its desired implantation site. Typically, when these pressure-expandable endoluminal devices are mounted on a balloon catheter, the balloon is initially deflated and furled, twisted or twined to a small diameter, to allow the radially compact endoluminal device to be mounted thereon. Subsequent inflation of the balloon will then cause the endoluminal device to radially expand, to its radially expanded, operative diameter.

In some procedures, it is important that the endoluminal device be prevented from rotating or undergoing torsional deformation as it is being expanded from its radially compact configuration, to its radially expanded configuration. Such prevention of rotation or torsional deformation is particularly important when precise rotational orientation of the endoluminal device must be maintained.

One example of a procedure wherein precise rotational orientation of an endoluminal device is critical, is the deployment of a modular endoluminal graft within a bifurcated or branched segment of a blood vessel (e.g., within the aorto-iliac bifurcation to treat an infrarenal aortic aneurysm which involves the iliac arteries). In such procedures, a primary graft is initially implanted within one of the involved blood vessels (e.g., within the infrarenal aorta), such than one or more opening(s) formed in the primary graft is/are aligned with the other involved vessel(s) (e.g., with one or both of the iliac arteries). One or more secondary graft(s) is/are then implanted within the other involved blood vessel(s) (one or both of the iliac arteries) and such secondary graft(s) is/are connected to the corresponding opening(s) formed in the primary graft. Thus, in these "modular" endovascular grafting procedures, it is important that the primary graft be positioned and maintained in a precise, predetermined rotational orientation to ensure that the opening(s) of the primary graft will be properly aligned with the other involved blood vessel(s). Any untoward rotation or torsional deformation of the primary graft during its radial expansion may result in nonalignment of the primary graft's opening(s) with the other involved vessel(s), and could render it difficult or impossible to subsequently connect the secondary graft(s) to the opening(s) in the primary graft, as desired.

Examples of modular endovascular grafts useable for aorto-iliac implantation as summarized above include those described in the following United States patents: U.S. Pat. No. 4,577,631 (Kreamer); U.S. Pat. No. 5,211,658 (Clouse); U.S. Pat. No. 5,219,355 (Parodi et al.); U.S. Pat. No. 5,316,023 (Palmaz et al.); U.S. Pat. No. 5,360,443 (Barone et al.); U.S. Pat. No. 5,425,765 (Tifenbrun et al.); U.S. Pat. No. 5,609,625; (Piplani et al.); U.S. Pat. No. 5,591,229 (Parodi et al.); U.S. Pat. No. 5,578,071 (Parodi); U.S. Pat. No. 5,571,173 (Parodi); U.S. Pat. No. 5,562,728 (Lazarus et al.); U.S. Pat. No. 5,562,726 (Chuter); U.S. Pat. No. 5,562,724 (Vorwerk et al.); U.S. Pat. No. 5,522,880 (Barone et al.); and U.S. Pat. No. 5,507,769 (Marin et al.).

In cases where a pressure-expandable endoluminal device is mounted upon and expanded by a balloon catheter (as described above), any significant rotation or torsional motion of the balloon during inflation, may result in corresponding rotation and/or torsion of the endoluminal device. This is especially true in cases where the balloon is relatively bulky, or of relatively large diameter, such as those balloons used to expand and implant endoluminal devices in large diameter vessels, such as the human aorta. Thus, the usual technique of furling, twining or twisting the deflated balloon prior to mounting of the endoluminal device thereon, may result in untoward rotation of torsional deformation of the expanding endoluminal device as the balloon is inflated.

Accordingly, there exists a need in the art for the development of new methods and/or devices for preventing rotation or torsional deformation of radially expandable endoluminal devices (e.g., stents, stented grafts, etc.) during implantation.

SUMMARY OF THE INVENTION

The present invention provides a method for forming countervailing folds in a deflated, catheter-mounted balloon to deter subsequent rotational movement or torsional deformation of a radially expandable endoluminal device which has been mounted upon the deflated balloon, and is expanded by inflation of the balloon.

In accordance with the method of the present invention, there is provided a balloon folding method which basically comprises the steps of:

a. forming a plurality of longitudinal furrows in the balloon, said longitudinal furrows defining balloon portions therebetween; and, b. folding each balloon portion a first time, in a first direction, to thereby form singly-over-folded balloon portions;

c. folding each balloon portion a second time, in a second direction, to thereby form doubly-over-folded balloon portions.

After completion of step c, the doubly-over-folded balloon portions may optionally be overlapped with one another. Also, a compressive outer jacket (e.g., a tape wrap or a tubular sleeve) may optionally be applied to compress or flatten the folded balloon prior to mounting of the radially expandable endoluminal device on the balloon.

Further in accordance with the invention, there is provided a system for implanting a radially expandable endoluminal device within a luminal anatomical structure (e.g., a blood vessel). The system generally comprises a) a catheter having a deflated balloon mounted thereon and b) an endoluminal device mounted on said deflated balloon in a radially compact state, said device being radially expandable to an expanded state upon inflation of said balloon. The catheter balloon is folded in accordance with the above-summarized balloon folding method of the present invention. The endoluminal device mounted on the balloon may be any suitable type of radially expandable device, including but not necessarily limited to stents, grafts, stented grafts, and other radially expandable intraluminal apparatus.

Further objects and advantages of the present invention will become apparent to those skilled in the relevant art upon reading and understanding the following detailed description and the accompanying drawings.

BRIEF DESCRIPTION OF THE DRAWINGS

FIG. 1a is a partial elevational view of the distal portion of a delivery catheter having a foldable balloon of the present invention mounted thereon in its deflated state.

FIG. 1b is an elevational view of a portion of a delivery catheter having a balloon of the present invention, in its inflated state.

FIG. 2e is a cross-sectional view through line 2a—2a of FIG. 1b showing a fourth step in the folding of the balloon in accordance with the present invention.

FIG. 2f is a cross-sectional view through line 2a—2a of FIG. 1b showing the final step in the folding of the balloon in accordance with the present invention.

FIG. 2g is a cross-sectional view through line 2a—2a of FIG. 1b showing the folded balloon of FIG. 2f after a pressure-exerting rapping has been applied thereto, in accordance with the present invention.

DETAILED DESCRIPTION OF THE PREFERRED EMBODIMENT

Figure 2A:
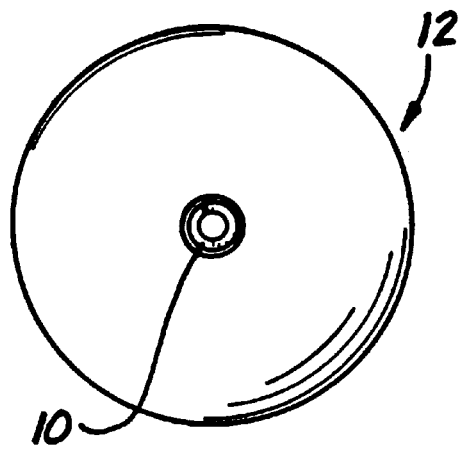
FIG. 2a is a cross-sectional view through line 2a—2a of FIG. 1b.

The following detailed description and the accompanying drawings to which it refers are provided for the purpose of describing presently preferred embodiments and/or examples of the invention only, and are not intended to limit the scope of the invention in any way.

FIGS. 1a and 1b show a balloon catheter of the present invention, comprising an elongate pliable catheter body 10 which has a balloon 12 mounted thereon. A balloon inflation lumen (not shown) extends through the catheter body to permit inflation fluid to be passed into, and withdrawn from, the balloon 12. FIG. 1a shows the balloon 12 in a collapsed state after having been folded in accordance with the present invention, while FIG. 1b shows the same balloon 12 in its fully inflated state.

As best appreciated from the showing of FIG. 1b, the balloon preferably comprises a generally cylindrical side wall 14, a tapered proximal end wall 16a, a portion of which is fused to the catheter body 10 at the proximal end of the balloon 12, and a tapered distal end wall 16b, a portion of which is fused to the catheter body 10 at the distal end of the balloon 12. The balloon 12 may be formed of any suitable material. In some applications, the balloon 12 may preferably be formed of polyethylene teraphthalate (PET) or may alternatively be formed of nylon or other suitable material.

One example of a balloon which is foldable in accordance with the present invention is that described in copending U.S. patent application Ser. No. 08/713,070 entitled Endovascular Delivery System. However, it will be appreciated that the balloon folding technique of the present invention will be useable with various types of balloons, as are used to radially expand various types of radially expandable intraluminal devices (e.g., stents, stented grafts, etc.).

The preferred method of folding the balloon 12 is shown in step-by-step fashion in FIGS. 2a–2g. As shown in FIG. 2a, the balloon 12 is initially deployed in its fully inflated configuration wherein the cylindrical sidewall 14 of the balloon 12 is disposed radially about a longitudinal axis LA which is projectable through the balloon 12 as shown in FIG. 1b.

Figure 2B:
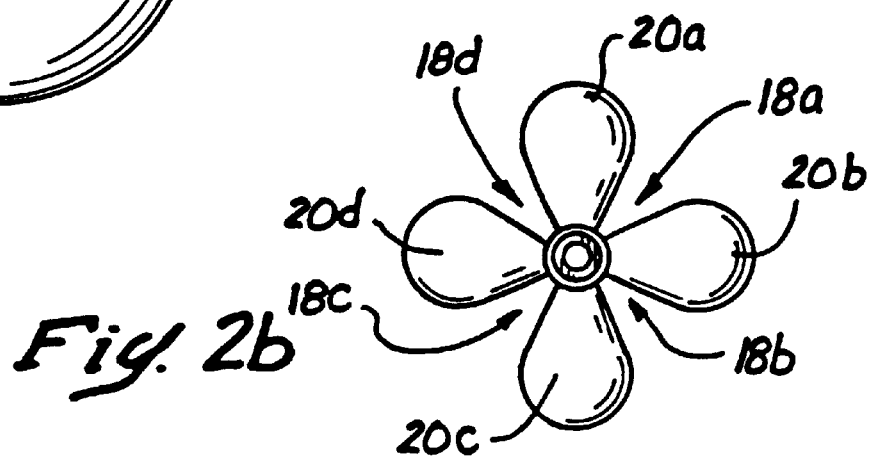
FIG. 2b is a cross-sectional view through line 2a—2a of FIG. 1b, showing a first step in folding of the balloon in accordance with the present invention.

As shown in FIG. 2b, a plurality of longitudinal furrows 18 (e.g., depressions, grooves, indentations, infoldings, invaginations, etc.) are formed in the sidewall 14 of the balloon 12, so as to define a plurality of balloon portions 20 between such longitudinal furrows 18. Such furrows 18 are preferably parallel, or substantially parallel, to the longitudinal axis LA of the balloon. Also, it is preferable that an even number of these longitudinal furrows 18 be formed in the balloon 12. In most cases, there will be a total of two (2), four (4) or six (6) longitudinal furrows 18 formed. In the particular example shown in the drawings, a total of four (4) longitudinal furrows 18a, 18b, 18c and 18d have been formed at equally spaced locations (e.g., 90 degrees, 180 degrees, 270 degrees and 360 degrees) about the sidewall 14 of the balloon 12. The formation of these four (4) longitudinal furrows 18a, 18b, 18c, and 18d has served to define a total of four (4) balloon portions 20a, 20b, 20c and 20d, between the respective furrows 18a, 19b, 18c and 18d.

Figure 2C:
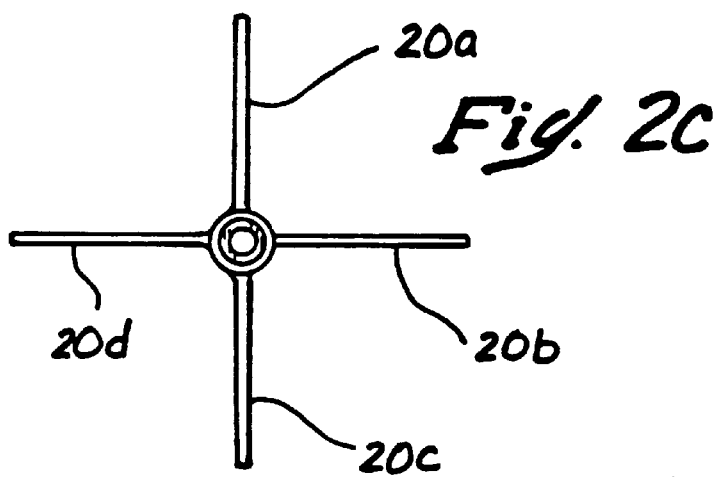
FIG. 2c is a cross-sectional view through line 2a—2a of FIG. 1b showing a second step in the folding of the balloon in accordance with the present invention.

Thereafter, as shown in FIG. 2c, each balloon portion 20a, 20b, 20c and 20d is pressed or collapsed into a flattened configuration.

Figure 2D:
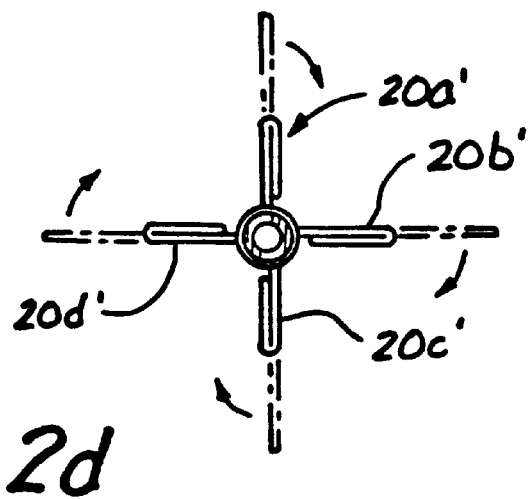
FIG. 2d is a cross-sectional view through line 2a—2a of FIG. 1b showing a third step in the folding of the balloon in accordance with the present invention.

Thereafter, each balloon portion 20a, 20b, 20c and 20d is overfolded, a first time, in the clockwise direction. (i.e. the direction indicated by the arrows shown in FIG. 2d). Such overfolding of the balloon portions 20a, 20b, 20c and 20d results in the formation of singly folded balloon portions 20a', 20b', 20c' and 20d', as shown in FIG. 2d.

Thereafter, each singly folded balloon portion 20a', 20b', 20c' and 20d' is overfolded, in the counterclockwise direction (i.e., the direction indicated by the arrows in FIG. 2e). Such overfolding of the singly folded balloon portions 20a', 20b', 20c' and 20d' results in the formation of doubly folded balloon portions 20a", 20b", 20c" and 20d", as shown in FIG. 2e.

Thereafter, if the mass of the balloon material permits, the doubly folded balloon portions 20a", 20b", 20c" and 20d" may be placed in alternating, overlapping disposition as shown in FIG. 2f. Such alternating, overlapping disposition may be achieved by causing the second and forth doubly folded balloon portions 20b", 20d" to lay over (e.g.,to bend or curl) in the counterclockwise direction, and subsequently causing the first and third doubly folded balloon portions 20a", 12c" to lay over (e.g.,to bend or curl) in the clockwise direction, such that they overlap in the manner shown in FIG. 2f.

Thereafter, a compressive jacket 24 is then formed about the balloon, to compress and flatten the balloon material. Depending on what material the balloon 12 is formed of, it may also be desirable to apply heat to the compressive jacket 24 to facilitate compression and/or flattening of the balloon material. Such compressive jacket 24 may comprise a wrapping of tape or other material about the balloon 12. Such wrapping may be accomplished by helically winding a strip or ribbon of plastic tape such as tape formed of polytetrafluoroethylene (PTFE), polyester, polypropylene or other suitable plastic for compressive wrapping about the balloon 12. Alternatively such compressive jacketing of the balloon 12 may be accomplished by advancing a tubular sleeve formed of material such as polyolefin, PVC or other suitable plastic, over the folded balloon 12 to form a compressive outerjacket 24 thereon. The compressive outer jacket 24 is then allowed to remain on the balloon 12 long enough to compress the balloon 12 sufficiently to permit the desired intraluminal device (e.g., stent, stented graft, etc.) to be mounded thereupon, in a radially collapsed configuration. Preferably, the intraluminal device is mounted on the compressed balloon 12 in a radially collapsed state of small enough diameter to allow the catheter 10 (with the radially compressed intraluminal device mounted thereon) to be transluminally advanced into the particular anatomical conduit in which the intraluminal device is to be implanted. It is to be appreciated that the invention has been described hereabove with reference to certain presently preferred embodiments or examples as shown in the drawings, and no effort has been made to exhaustively describe each and every embodiment in which the invention may exist. Indeed, numerous modifications could be made to the above-described embodiments without departing form the intended spirit and scope of the invention and it is intended that all such modifications be included within the scope of the following claim.

What is claimed is:

1. A system for implanting a radially expandable endoluminal device within a luminal anatomical structure, said system comprising:

a catheter having a deflated balloon mounted thereon;

an endoluminal device mounted on said deflated balloon in a radially compact state, said device being radially expandable to an expanded state upon inflation of said balloon;

said balloon being folded by a method which comprises the steps of:

a. forming a plurality of longitudinal furrows in the balloon, said longitudinal furrows defining balloon portions therebetween;

b. folding each balloon portion a first time, in a first direction, to thereby form singly-over-folded balloon portions; and, c. folding each balloon portion a second time, in a second direction, to thereby form doubly-over-folded balloon portions.

2. The system of claim 1 wherein the method by which the balloon is folded further comprises the step of:

d. causing the doubly-folded balloon portions to overlap one another.

3. The system of claim 2 wherein the method by which the balloon is folded further comprises the step of:

e. placing a compressive jacket about the doubly-folded, overlapping balloon portions to compress the balloon prior to mounting the radially expandable intraluminal device thereon.

4. The system of claim 3 wherein step e of the method by which the balloon is folded comprises:

helically wrapping a tape about the balloon to form a compressive outer jacket thereon.

5. The system of claim 3 wherein step e of the method by which the balloon is folded comprises:

advancing a tubular sleeve onto said balloon to form a compressive outer jacket thereon.

6. The system of claim 1 wherein the method by which the balloon is folded further comprises the step of:

d. placing a compressive jacket about the doubly-folded balloon portions to compress the balloon prior to mounting of the radially expandable intraluminal device thereon.

7. The system of claim 1 wherein step d of the method by which the balloon is folded comprises:

helically wrapping a tape about the balloon to form a compressive outer jacket thereon.

8. The system of claim 1 wherein step d of the method by which the balloon is folded comprises:

advancing a tubular sleeve onto said balloon to form a compressive outer jacket thereon.

9. The system of claim 1 wherein two longitudinal furrows are formed in the balloon in step a of the balloon folding method, thereby defining first and second balloon portions.

10. The system of claim 1 wherein four longitudinal furrows are formed in the balloon in step a of the balloon folding method, thereby defining first, second, third and fourth balloon portions.

11. The system of claim 1 wherein six longitudinal furrows are formed in the balloon in step a of the balloon folding method, thereby defining first, second, third, fourth, fifth and sixth balloon portions.

12. The system of claim 1 wherein step c of the method by which the balloon is folded further comprises:

flattening of said balloon portions prior to folding said balloon portions for the first time.

13. The system of claim 1 wherein the endoluminal device is a pressure-expandable endoluminal device.

14. The system of claim 13 wherein the radially expandable endoluminal device is selected from the group of radially expandable endoluminal devices consisting of:

stents;

grafts;

stented grafts; and, radially expandable intraluminal apparatus.

15. A system for implanting a radially expandable endoluminal device within a luminal anatomical structure, said system comprising:

a catheter having a deflated balloon mounted thereon;

an endoluminal device mounted on said deflated balloon in a radially compact state, said device being radially expandable to an expanded state upon inflation of said balloon;

said balloon including a sidewall and a plurality of longitudinal furrows formed in the sidewall defining balloon portions therebetween, each balloon portion including two layers of said sidewall and being doubly-over-folded on itself to form a doubly folded portion including eight layers of said sidewall.

16. The system of claim 15 wherein the doubly folded portions overlap one another.

17. The system of claim 15 further including:

a compressive jacket positioned about the doubly folded portions to compress the balloon, enabling mounting of the radially expandable intraluminal device thereon.

18. The system of claim 17 wherein the compressive outerjacket comprises a helically wrapped tape.

19. The system of claim 17 wherein the compressive outerjacket comprises a tubular sleeve.

20. The system of claim 15 wherein there are just two of the longitudinal furrows formed in the balloon, thereby defining first and second balloon portions.

21. The system of claim 15 wherein there are four of the longitudinal furrows formed in the balloon, thereby defining first, second, third and fourth balloon portions.

22. The system of claim 15 wherein there are six of the longitudinal furrows formed in the balloon, thereby defining first, second, third, fourth, fifth and sixth balloon portions.

23. The system of claim 15 wherein the balloon portions are flattened prior to folding them for the first time.

24. The system of claim 15 wherein the balloon portions are folded first in one clock sense to form singly folded portions and then in the other clock sense to form to form the doubly folded portions.

25. The system of claim 24 wherein the singly folded portions are formed by folding the balloon portions in approximately half, and the doubly folded portions are formed by folding the singly folded portions in approximately half.

26. A balloon catheter having a distal region, a deflated balloon attached to the balloon catheter in the distal region of the catheter, the balloon having a thin wall, said balloon further having a plurality of longitudinal furrows along a substantial portion of its length, each of said furrows having adjacent balloon portions on either side of the furrow, said balloon portions being formed of two layers of the thin wall of the balloon, wherein each of said balloon portions is doubled over on itself in a first direction to form an intermediate node configuration, each intermediate node comprising four layers of he wall thickness of the balloon, each intermediate node being further doubled over on itself in a second direction opposite to the first direction to form a final node configuration, with the final node configuration comprising eight layers of the thin wall of the balloon.

27. A balloon angioplasty catheter having a distal section and having an inflatable multifold balloon situated at the catheters distal section, the multifold balloon having a thin wall, the balloon having at its longitudinal center at least three folded nodes when in a compressed state prior to balloon inflation with each folded node comprised of folding of the balloon first in one direction and then the opposite direction so that each one of the at least three folded nodes comprises multiple layers of the thin wall of the balloon.

28. A multifold balloon endoluminal prosthesis delivery catheter comprising;

a balloon catheter having a distal section and having an inflatable multifold balloon situated at the catheters distal section, the multifold balloon having a thin wall, the balloon having at its longitudinal center at least tree folded nodes when in a compressed state prior to balloon inflation with each folded node consisting of folding of the balloon's thin wall first in one direction and then the opposite direction so that each one of the at least three folded nodes comprises multiple layers of the thin wall of the balloon; and, an endoluminal device placed onto the multifold balloon of the balloon catheter, the endoluminal device configured to have a first radially compact cross section upon placement on the multifold balloon, and a second radially expanded cross section upon inflation of the multifold balloon.

29. A method for folding a catheter mounted balloon which has a generally cylindrical sidewall, and is used to radially expand an intraluminal device which has been mounted on the balloon, said method comprising the steps of:

a. forming a plurality of longitudinal furrows in the balloon, said longitudinal furrows defining balloon portions therebetween; and, b. folding each balloon portion a first time, in a first direction, to thereby form singly-over-folded balloon portions;

c. folding each balloon portion a second time, in a second direction, to thereby form doubly-over-folded balloon portions.

30. The method of claim 1 further comprising the step of:

d. causing the doubly-folded balloon portions to overlap one another.

31. The method of claim 30 wherein the method further comprises the step of:

e. placing a compressive jacket about the doubly-folded, overlapping balloon portions to compress the balloon prior to mounting the radially expandable intraluminal device thereon.

32. The method of claim 31 wherein step e comprises:

helically wrapping a tape about the balloon to form a compressive outer jacket thereon.

33. The method of claim 31 wherein step e comprises:

advancing a tubular sleeve onto said balloon to form a compressive outer jacket thereon.

34. The method of claim 1 wherein the method further comprises the step of:

d. placing a compressive jacket about the doubly-folded balloon portions to compress the balloon prior to mounting of the radially expandable intraluminal device thereon.

35. The method of claim 34 wherein step d comprises:

helically wrapping a tape about the balloon to form a compressive outer jacket thereon.

36. The method of claim 34 wherein step d comprises:

advancing a tubular sleeve onto said balloon to form a compressive outer jacket thereon.

37. The method of claim 1 wherein two longitudinal furrows are formed in the balloon in step a, thereby defining first and second balloon portions.

38. The method of claim 1 wherein four longitudinal furrows are formed in step a, thereby defining first, second, third and fourth balloon portions.

39. The method of claim 1 wherein six longitudinal furrows are formed in step a, thereby defining first, second, third, fourth, fifth and sixth balloon portions.

40. The method of claim 1 wherein step c further comprises:

flattening of said balloon portions prior to folding said balloon portions for the first time.

* * * * *